United States Patent
Ho et al.

(10) Patent No.: US 8,365,731 B2
(45) Date of Patent: Feb. 5, 2013

(54) PRESSURE REDUCING VALVE WITH FLEXIBLE CUFF

(75) Inventors: Peter Chi Fai Ho, Pittsburgh, PA (US); Lance Busch, Trafford, PA (US)

(73) Assignee: Ric Investments, LLC, Wilmington, DE (US)

( * ) Notice: Subject to any disclaimer, the term of this patent is extended or adjusted under 35 U.S.C. 154(b) by 1103 days.

(21) Appl. No.: 12/169,658

(22) Filed: Jul. 9, 2008

(65) Prior Publication Data

US 2009/0032022 A1 Feb. 5, 2009

Related U.S. Application Data

(60) Provisional application No. 60/953,001, filed on Jul. 31, 2007.

(51) Int. Cl.
*A62B 9/02* (2006.01)

(52) U.S. Cl. ......... 128/205.24; 128/204.18; 128/205.28; 137/102

(58) Field of Classification Search ............. 128/204.18, 128/204.23, 204.26, 205.24, 205.27, 205.28, 128/206.12, 206.15, 206.21, 207.12; 137/102
See application file for complete search history.

(56) References Cited

U.S. PATENT DOCUMENTS

| | | | |
|---|---|---|---|
| 5,002,050 A | 3/1991 | McGinnis | |
| 5,163,424 A | 11/1992 | Kohnke | |
| 5,501,214 A | 3/1996 | Sabo | |
| 5,813,401 A | 9/1998 | Radcliff et al. | |
| 5,878,743 A | 3/1999 | Zdrojkowski et al. | |
| 5,896,857 A | 4/1999 | Hely et al. | |
| 5,937,855 A | 8/1999 | Zdrojkowski | |
| 6,105,575 A | 8/2000 | Estes et al. | |
| 6,253,764 B1 | 7/2001 | Calluaud | |
| 6,766,800 B2 | 7/2004 | Chu et al. | |
| 6,923,181 B2 * | 8/2005 | Tuck | 128/205.24 |
| 7,063,086 B2 | 6/2006 | Shahbazpour et al. | |
| 7,066,174 B1 * | 6/2006 | Smith et al. | 128/205.24 |
| 2003/0066530 A1 * | 4/2003 | Shahbazpour et al. | 128/205.24 |
| 2004/0255948 A1 * | 12/2004 | Smith et al. | 128/206.15 |
| 2006/0076017 A1 * | 4/2006 | Walker et al. | 128/205.24 |
| 2008/0078395 A1 * | 4/2008 | Ho et al. | 128/205.24 |

* cited by examiner

*Primary Examiner* — Loan Thanh
*Assistant Examiner* — Kathryn D Sheikh
(74) *Attorney, Agent, or Firm* — Michael W. Haas

(57) ABSTRACT

A pressure reducing valve for use in a system adapted to deliver a breathing gas to a patient. The pressure reducing valve is structured to communicate a flow of breathing gas to such a patient's airway during an inspiratory phase. The pressure reducing valve is structured to discharge the flow of breathing gas and a flow of exhaled gas to atmosphere during the expiratory phase. The flow of breathing gas and flow of exhaled gas are discharged to atmosphere through a number of exhaust ports. Because the flow of breathing gas and flow of exhalation gas are discharged through the exhaust ports, less effort is required by a patient during the expiratory phase.

35 Claims, 12 Drawing Sheets

PRESSURE REDUCING VALVE WITH FLEXIBLE CUFF

CROSS-REFERENCE TO RELATED APPLICATIONS

This application claims priority under 35 U.S.C. §119(e) from provisional U.S. patent application No. 60/953,001 filed 31 Jul. 2007, the entire contents of which are incorporated herein by reference.

BACKGROUND OF THE INVENTION

1. Field of the Invention

The present invention pertains to the delivery of a flow of breathing gas to the airway of a patient and more particularly to an apparatus and method for providing improved comfort for a patient receiving a flow of breathing gas.

2. Description of the Related Art

There are numerous situations where it is necessary or desirable to deliver a flow of breathing gas to the airway of a patient. For example, it is known to deliver a flow of breathing gas to a patient during at least a portion of the breathing cycle to treat breathing and/or cardiac disorders such as obstructive sleep apnea syndrome, chronic obstructive pulmonary disease, congestive heart failure, and other respiratory and/or breathing disorders.

While sleeping, a patient suffering from obstructive sleep apnea syndrome (OSAS) is prone to having their airway narrow and/or collapse due to, for instance, mechanical collapsing forces that result from the structure of the airway tissues, poor muscle tone, and body position. One method of treating OSAS is continuous positive airway pressure (CPAP) therapy. With CPAP therapy, a flow of breathing gas is supplied at a constant pressure of sufficient magnitude to splint the patient's airway open and to prevent the narrowing and/or collapse of the airway.

During a normal breathing cycle, however, the pressure gradient between the lungs and the exterior of the body is not constant. For example during inspiration, the pressure gradient (sometimes referred to as the "inspiratory pressure gradient") falls from zero at the start of the inspiratory phase to a peak negative value and then rises back to zero at the end of the inspiratory phase. During expiration, the pressure gradient (sometimes referred to as the "expiratory pressure gradient") rises from zero at the start of the expiration phase to a peak value and then falls back to zero at the end of the expiratory phase. Because the pressure gradient varies over the breathing cycle, ideally the pressure necessary to overcome airway collapse should vary accordingly over the breathing cycle. Thus, although CPAP provides a simple treatment solution for OSAS, the application of a constant splinting pressure to the airway exposes the patient to pressures that are higher than the pressures needed to support the airway for most of the breathing cycle.

Advanced therapies, such as bi-level positive airway pressure (bi-level PAP) therapies and proportional positive airway pressure therapies, seek to take advantage of the different pressure requirements and lower the pressure at certain instances during the breathing cycle. In bi-level PAP therapy, for example, a flow of breathing gas is supplied to a patient's airway at a first pressure during the inspiratory phase and a flow of breathing gas at a lower pressure is supplied to the patient's airway during the expiratory phase. These advanced therapies, however, may cause discomfort because the patient must still overcome the resistance created by the low pressure flow of breathing gas supplied during the expiratory phase.

Accordingly, a need exists for an apparatus and method for providing improved comfort for a patient receiving a flow of breathing gas which overcomes these and other problems associated with known systems.

SUMMARY OF THE INVENTION

In accordance with an aspect of the present invention, a pressure reducing valve comprises a valve body and a flexible cuff. The valve body has a first end, a second end, and a number of exhaust ports therebetween. The flexible cuff is adapted to alternate between a first position in which the number of exhaust ports are substantially closed and a second position in which the number of exhaust ports are substantially open. When the flexible cuff is in the first position, the pressure reducing valve is structured to fluidly communicate a flow of breathing gas from the first end to the second end. When the flexible cuff is in the second position, the pressure reducing valve is structured to fluidly communicate the flow of breathing gas from the first end to the number of exhaust ports and fluidly communicate a flow of exhaled gas from the second end to the number of exhaust ports.

According to another aspect of the present invention, a pressure reducing valve comprises a valve body having a patient interface end and a pressure generator end with a number of exhaust ports therebetween and a flexible cuff actuatable within the valve body. The flexible cuff is structured to allow communication of a flow of breathing gas from the pressure generator end to the patient interface end during a breathing cycle inspiratory phase, and structured to allow communication of the flow of breathing gas and a flow of exhaled gas through the number of exhaust ports during a breathing cycle expiratory phase.

According to another aspect of the present invention, a method for ventilating a patient comprises establishing a patient circuit between a pressure generating device and an airway of a patient, communicating a flow of the breathing gas through the patient circuit to the airway of such patient during an inspiratory stage, and diverting the flow of the breathing gas and directing a flow of exhaled gas away from the airway of such patient during an expiratory phase. The patient circuit includes a pressure reducing valve comprising a valve body with a first end, a second end, and a number of exhaust ports therebetween and a flexible cuff adapted to alternate between a first position in which the number of exhaust ports are substantially closed and a second position in which the number of exhaust ports are substantially open. While the flexible cuff is in the first position, the pressure reducing valve is structured to fluidly communicate the flow of breathing gas from the first end to the second end. While the flexible cuff is in the second position, the pressure reducing valve is structured to fluidly communicate, to the number of exhaust ports, the flow of breathing gas from the first end and the flow of exhaled gas from the second end.

According to another aspect of the present invention, a system adapted to provide a regimen of respiratory therapy to a patient comprises a pressure generating device structured to produce a flow of breathing gas, a patient interface device structured to communicate the flow of breathing gas to the airway of a patient and to communicate a flow of exhaled gas from the airway of such patient, a patient circuit structured to fluidly couple the pressure generating device to the patient interface device, and a pressure reducing valve disposed between the pressure generating device and the patient interface device. The pressure reducing valve comprises a valve body with a number of exhaust ports therein, and a flexible cuff structured to alternate between a first position in which the flow of breathing gas is communicated from the pressure generating device to the patient interface device, and a second position, in which the flow of breathing gas from the pressure generating device and the flow of exhaled gas from the patient interface device are discharged through the number of exhaust ports.

According to another aspect of the present invention, an apparatus for delivering a flow of breathing gas to an airway of a patient comprises a pressure generating means for producing the flow of breathing gas, a patient interface means for communicating the flow of breathing gas to the airway of a patient and for communicating a flow of exhaled gas from the airway of such patient, and a patient circuit structured to fluidly couple the pressure generating means to the patient interface means. The patient circuit includes a pressure reducing valve which comprises a valve body, with a number of exhaust ports therein, and a flexible cuff means for alternating between a first position, in which the flow of breathing gas is communicated from the pressure generating means to the patient interface means, and a second position, in which the flow of breathing gas from the pressure generating means and the flow of exhaled gas from the patient interface means are discharged through the number of exhaust ports These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
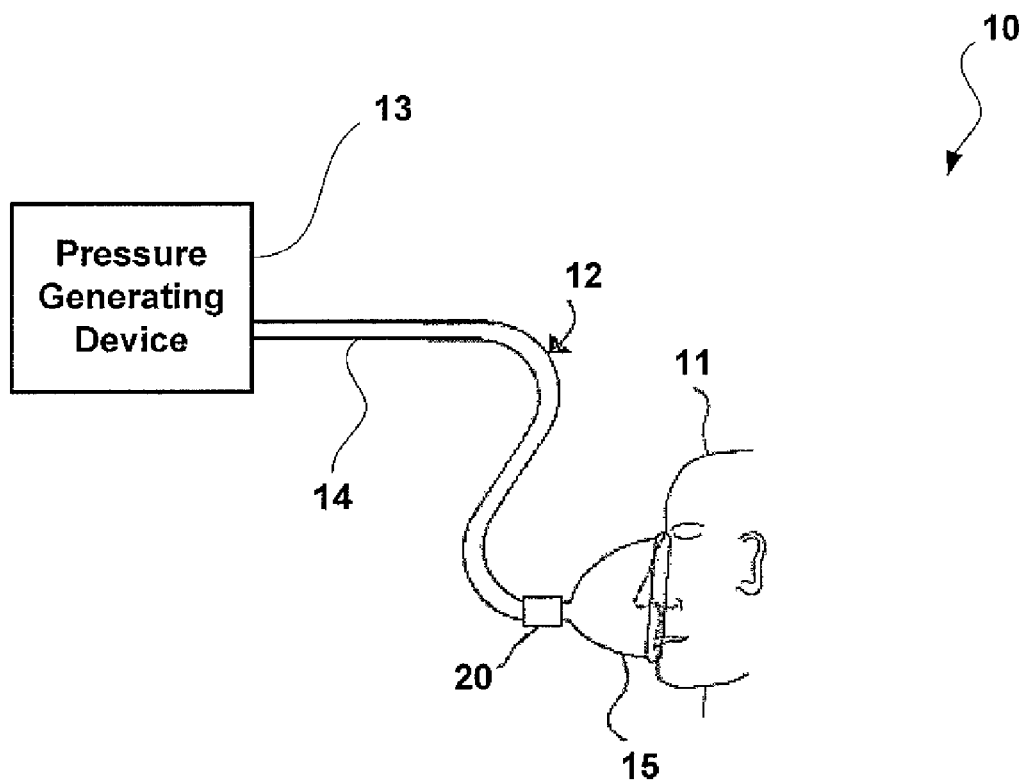
FIG. 1 is a schematic view of a system adapted to provide a regimen of respiratory therapy to a patient according to one embodiment.

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

A system 10 adapted to provide a regimen of respiratory therapy to a patient 11 according to one embodiment is generally shown in FIG. 1. System 10 includes a pressure generating device 13, a patient circuit 12, and a patient interface device 15. Pressure generating device 13 is structured to generate a flow of breathing gas and may include, without limitation, a ventilator, a pressure support device (such as a continuous positive airway pressure device, or CPAP device), a variable pressure device (e.g., a BiPAP® device, a Bi-Flex® device, or a C-Flex™ device, each of which are manufactured and distributed by Respironics, Inc. of Murrysville, Pa.), an auto-titration pressure support system, a compressed air source, and/or a bottled gas source.

Patient circuit 12 is structured to communicate the flow of breathing gas from pressure generating device 13 to patient interface device 15. In the current embodiment, patient circuit 12 includes a conduit 14 and a pressure reducing valve 20 which, as will be discussed in more detail herein, is adapted to provide a pressure reduction effect at certain instances during a patient's breathing cycle.

Patient interface 15 is typically a nasal mask or a full face mask (i.e., a nasal/oral mask) structured to be placed on and/or over the face of patient 11. Any type of patient interface device 15, however, which facilitates the delivery of the flow of breathing gas communicated from pressure generating device 13 to the airway of patient 11 may be used while remaining within the scope of the present invention. For example, a nasal cannula, a total face mask, or an endotracheal tube may be used in addition to a nasal mask or a full face mask.

Generally, pressure reducing valve 20 is disposed in patient circuit 12 between pressure generating device 13 and patient interface device 15. As shown in FIG. 1, for instance, patient interface 15 is coupled directly with pressure reducing valve 20, which is coupled with one end of conduit 14. The opposite end of conduit 14 is coupled with pressure generating device 13. Other arrangements, however, are contemplated as falling within the scope of the present invention. For example, pressure reducing valve 20 may be coupled to an outlet of pressure generating device 13. Furthermore, it is contemplated that pressure reducing valve 20 may be integrated into one of pressure generating device 13, conduit 14, or patient interface device 15. Accordingly, as used herein the terminology "disposed between" encompasses any arrangement in which pressure reducing valve 20 is located between an inlet of pressure generating device 13 and the cushion of patient interface 15.

FIGS. 2-8 illustrate various embodiments of a pressure reducing valve for use with a system adapted to provide a regimen of respiratory therapy to a patient, such as and without limitation, system 10. In each embodiment, the pressure reducing valve includes a valve body and a flexible cuff. The pressure reducing valve is structured to communicate a flow of breathing gas to a patient's airway during the inspiratory phase of the breathing cycle and is structured to discharge, for instance to atmosphere, the flow of breathing gas and a flow of exhaled gas through a number of exhaust ports during the expiratory phase of the breathing cycle. Because the flow of breathing gas and flow of exhalation gas are discharged through a number of exhaust ports, less effort is required by a patient during the expiratory phase.

As employed herein, a pressure reducing valve is said to be in a "first position" or "open" when the flexible cuff allows a flow of breathing gas to pass from the pressure generating end to the patient interface end while simultaneously occluding flow through a number of exhaust ports. A pressure reducing valve is typically in the first position during an inspiratory phase (i.e., when a patient is inhaling). As employed herein, a pressure reducing valve is said to be in a "second position" or "closed" when the flexible cuff does not occlude a flow of breathing gas and a flow of exhaled gas to be discharged through a number of exhaust ports. A pressure reducing valve is typically in the second position during an expiratory phase (i.e., when a patient is exhaling).

In effect, each embodiment of the pressure reducing valve of the present invention is structured to mechanically change a continuous pressure flow of breathing gas (e.g., a flow of breathing gas from a CPAP device) to a variable pressure flow of breathing gas (e.g., a flow of breathing gas from a bi-level and/or a C-FLEX™ device). Because the pressure reducing valve of the present invention uses the spontaneous response from the patient's breathing pattern to open and close the valve mechanically, the need for a pressure sensing device is eliminated. In contrast, the response of current bi-level devices at low supply pressures are limited by the sensitivity of the pressure sensing device. For example at low pressures, current bi-level devices produce an expiratory positive air pressure (EPAP) that is equal to the inspiratory positive air pressure (IPAP). To obtain an improved response, an expensive high sensitivity pressure sensing device must be used. It should be noted that each embodiment of the pressure reducing valve of the present invention, however, can convert a continuous pressure flow of breathing gas to a variable pressure flow of breathing gas over a full range of supply pressures. For example, each embodiment of the pressure reducing valve can convert a flow of breathing gas supplied by a CPAP device to a variable pressure flow of breathing gas, even at low pressures.

Figure 2A:
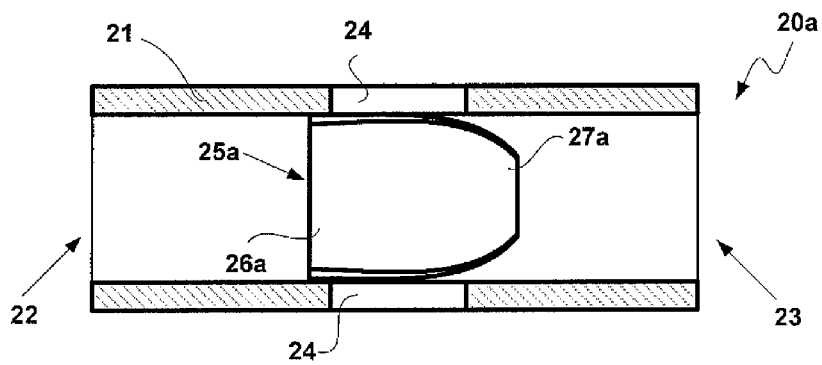
FIG. 2*a* is a cross-sectional view of a pressure reducing valve according to one embodiment.
Figure 2B:
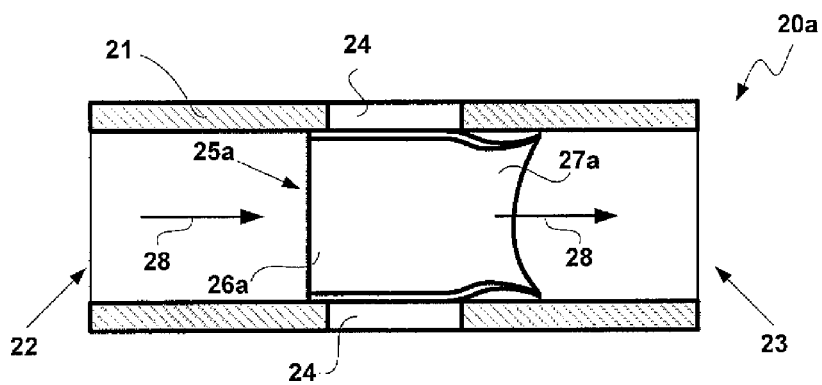
FIG. 2*b* shows the pressure reducing valve of FIG. 2*a* with the flexible cuff illustrated in a first position.
Figure 2C:
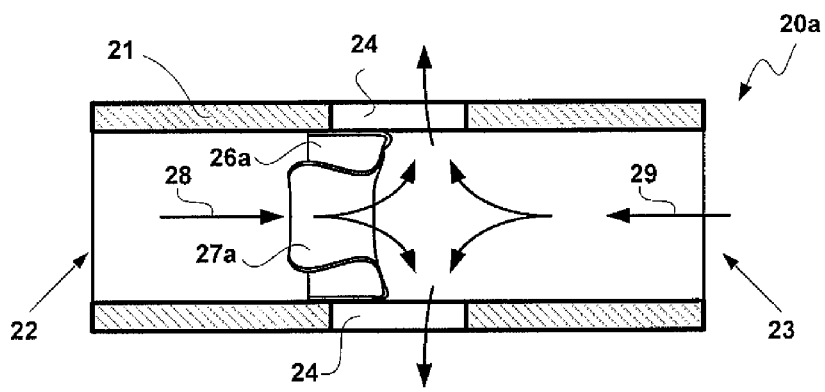
FIG. 2*c* shows the pressure reducing valve of FIG. 2*a* with the flexible cuff illustrated in a second position.

Referring now to FIGS. 2a-2c, a pressure reducing valve 20a according to one embodiment is illustrated. Pressure reducing valve 20a includes a valve body 21 and a flexible cuff 25a. Valve body 21 has a pressure generator end 22, a patient interface end 23, and a number of exhaust ports 24. Pressure generator end 22 is structured to receive a flow of breathing gas (as indicated by arrows 28 in FIGS. 2b and 2c) from a pressure generating device (not shown in FIGS. 2a-2c). For example pressure generator end 22 is adapted to couple with conduit 14 (see FIG. 1), which in turn, is adapted to couple with pressure generating device 13. Patient interface end 23 is structured to deliver flow of breathing gas 28 to the airway of a patient and/or to receive a flow of exhaled gas (as indicated by arrows 29 in FIG. 2c) from the airway of the patient. For example, patient interface end 23 is adapted to couple with patient interface device 15 (see FIG. 1) which is in fluid communication with the airway of patient 11.

Exhaust ports 24 are located between pressure generator end 22 and patient interface end 23. Exhaust ports 24 extend through the wall of valve body 21 allowing fluid communication between an interior and an exterior thereof. As will be discussed in more detail below, exhaust ports 24 are structured to allow flow of breathing gas 28 and flow of exhaled gas 29 to be communicated from the interior of valve body 21 to the exterior of valve body 21 when flexible cuff 25a is in a second position.

Flexible cuff 25a includes a first end 26a and a second end 27a. In the current embodiment, first end 26a is coupled to the interior of valve body 21. Accordingly, first end 26a remains stationary relative to valve body 21 when flexible cuff 25a alternates between a first position (FIG. 2b) and a second position (FIG. 2c).

During the inspiratory phase of a breathing cycle, flexible cuff 25a is in the first position. Referring to FIG. 2b, flexible cuff 25a substantially occludes exhaust ports 24 such that flow of breathing gas 28 is not discharged therethrough. Additionally, as seen in FIG. 2b, the second end 27a of flexible cuff 25a is structured to expand such that flow of breathing gas 28 flows more freely from pressure generating end 22 to patient interface end 23.

During the expiratory phase of a breathing cycle, flexible cuff 25a is in the second position. Referring to FIG. 2c, flow of exhaled gas 29 causes flexible cuff 25a to collapse such that second end 27a folds back (e.g., deforms and reverses) towards first end 26a. In this second position, exhaust ports 24 are open allowing flow of breathing gas 28 and flow of exhaled gas 29 to be discharged therethrough. Because flow of breathing gas 28 is discharged to atmosphere, the patient experiences a temporary drop in positive airway pressure. At the end of the expiratory phase, flow of exhaled gas 29 ceases, the patient begins to inhale, and flexible cuff 25a returns to the first position.

Figure 3A:
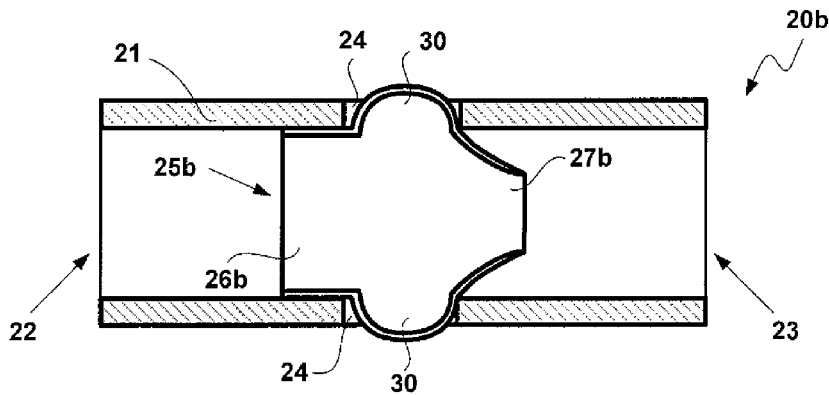
FIG. 3*a* is a cross-sectional view of a pressure reducing valve according to another embodiment.
Figure 3B:
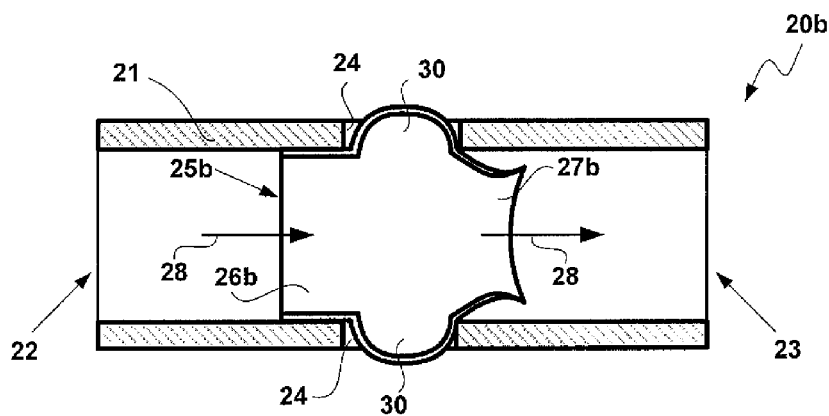
FIG. 3*b* shows the pressure reducing valve of FIG. 3*a* with the flexible cuff illustrated in a first position.
Figure 3C:
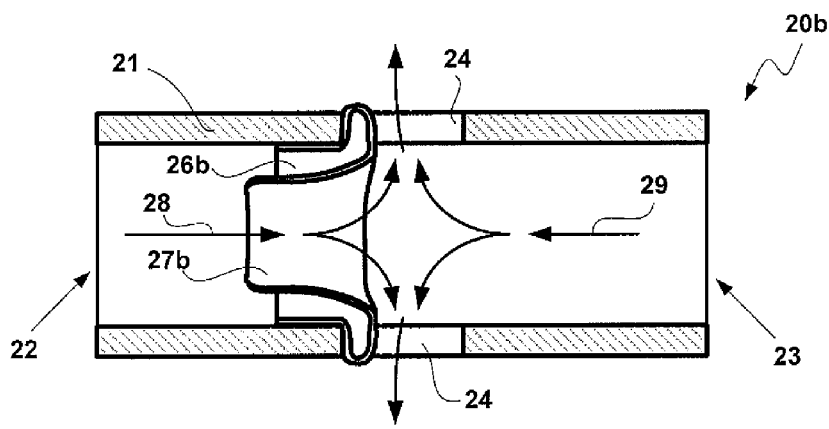
FIG. 3*c* shows the pressure reducing valve of FIG. 3*a* with the flexible cuff illustrated in a second position.

Referring now to FIGS. 3a-3c, a pressure reducing valve 20b according to another embodiment is illustrated. Pressure reducing valve 20b includes a valve body 21 and a flexible cuff 25b. Valve body 21 is substantially the same the valve body of pressure reducing valve 20a (e.g., has a pressure generating end 22, a patient interface end 23, and a number of exhaust ports therebetween).

Flexible cuff 25b includes a first end 26b and a second end 27b. In the current embodiment, first end 26b is coupled to the interior of valve body 21. Accordingly, first end 26b remains stationary relative to valve body 21 when flexible cuff 25b alternates between a first position (see FIG. 3b) and a second position (see FIG. 3c). Flexible cuff 25b also includes a bellows portion 30 between first end 26b and second end 27b.

During the inspiratory phase of a breathing cycle, as shown in FIG. 3b, flexible cuff 25b is in the first position. Bellows portion 30 substantially occludes exhaust ports 24 such that flow of breathing gas 28 is not discharged therethrough. Additionally, as seen in FIG. 3b, second end 27b of flexible cuff 25b is structured to expand such that flow of breathing gas 28 flows more freely from pressure generating end 22 to patient interface end 23.

During the expiratory phase of a breathing cycle, flexible cuff 25b is in the second position. Referring to FIG. 3c, flow of exhaled gas 29 causes flexible cuff 25b to collapse such that second end 27b folds back (e.g., deforms and reverses) towards first end 26b. In this second position, exhaust ports 24 are open allowing flow of breathing gas 28 and flow of exhaled gas 29 to be discharged therethrough. Because flow of breathing gas 28 is discharged to atmosphere, the patient experiences a temporary drop in positive airway pressure. At the end of the expiratory phase, flow of exhaled gas 29 ceases, the patient begins to inhale, and the flexible cuff 25b returns to the first position. In the current embodiment, bellows portion 30 is structured to generate a slight biasing force which assists the flexible cuff 25b in returning to the first position.

Figure 4A:
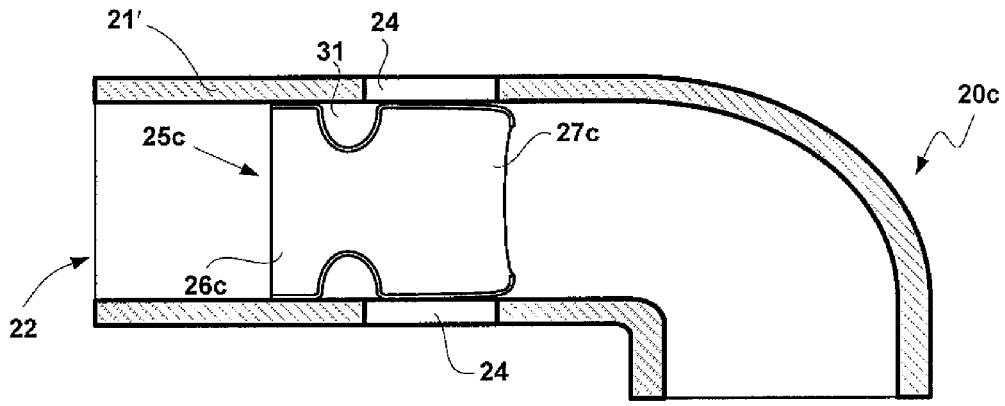
FIG. 4*a* is a cross-sectional view of a pressure reducing valve according to another embodiment.
Figure 4B:
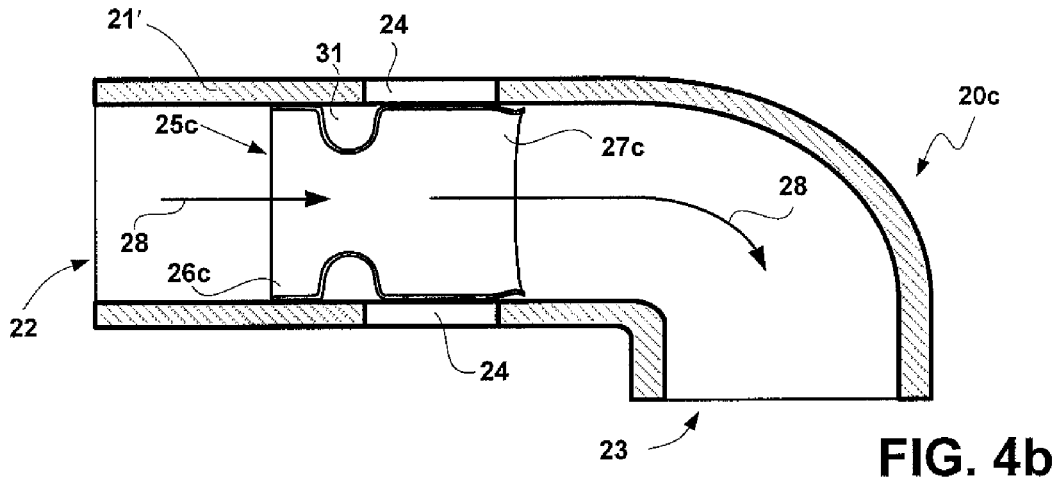
FIG. 4*b* shows the pressure reducing valve of FIG. 4*a* with the flexible cuff illustrated in a first position.
Figure 4C:
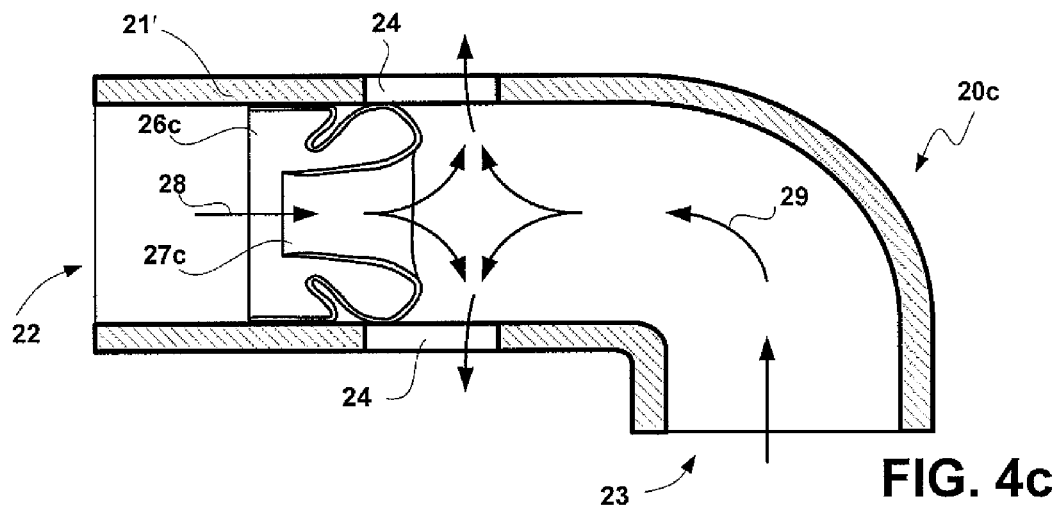
FIG. 4*c* shows the pressure reducing valve of FIG. 4*a* with the flexible cuff illustrated in a second position.

Referring now to FIGS. 4a-4c, a pressure reducing valve 20c according to another embodiment is illustrated. Pressure reducing valve 20c includes a valve body 21' having an elbow at patient interface end 23. This arrangement may be used, for example, to couple pressure reducing valve 20c directly to the shell of a patient interface device. Pressure reducing valve 20c also includes a pressure generating end 22 and a number of exhaust ports 24.

Flexible cuff 25c includes a first end 26c and a second end 27c. In the current embodiment, first end 26c is coupled to the interior of valve body 21'. Accordingly, first end 26c remains stationary relative to valve body 21' when flexible cuff 25c alternates between a first position (see FIG. 4b) and a second position (see FIG. 4c). In the current embodiment, flexible cuff 25c also includes a groove 31 between the first end 26c and the second end 27c. Groove 31 is adapted to lower the flexible cuff's resistance to folding, and thus allows flexible cuff 25 to collapse more readily in the presence of a flow of exhaled gas 29.

During the inspiratory phase of a breathing cycle, as shown in FIG. 4b, flexible cuff 25c is in the first position where exhaust ports 24 are occluded such that flow of breathing gas 28 is not discharged therethrough. Additionally, as seen in FIG. 4b, the second end 27c of flexible cuff 25c is structured to expand such that flow of breathing gas 28 flows more freely from pressure generating end 22 to patient interface end 23.

During the expiratory phase of a breathing cycle, flexible cuff 25c is in the second position. Referring to FIG. 4c, flow of exhaled gas 29 causes flexible cuff 25c to collapse such that second end 27c folds back (e.g., deforms and reverses) towards first end 26c. In this second position, exhaust ports 24 are opened allowing flow of breathing gas 28 and flow of exhaled gas 29 to be discharged therethrough. Because flow of breathing gas 28 is discharged to atmosphere, the patient experiences a temporary drop in positive airway pressure. At the end of the expiratory phase, flow of exhaled gas 29 ceases, the patient begins to inhale, and the flexible cuff 25c returns to the first position.

Figure 5A:
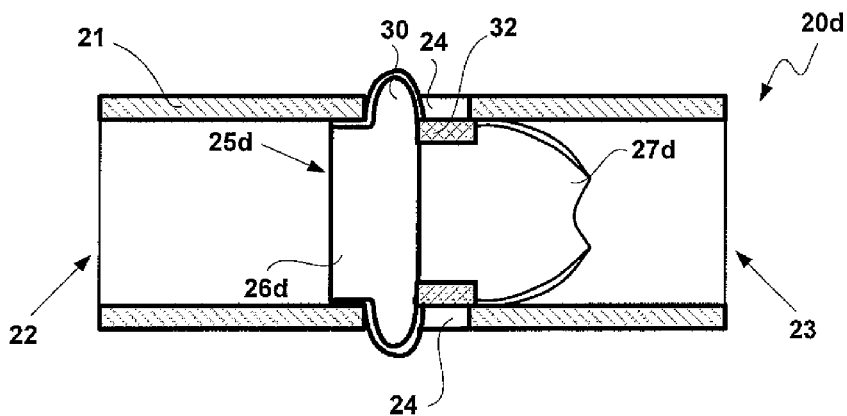
FIG. 5*a* is a cross-sectional view of a pressure reducing valve according to another embodiment.
Figure 5B:
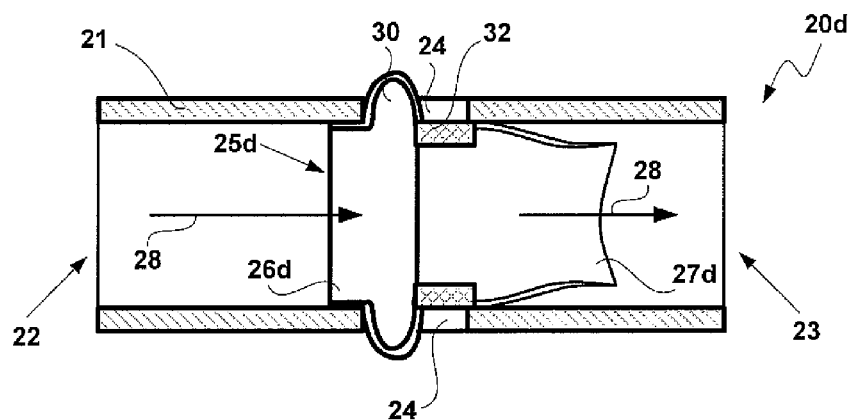
FIG. 5*b* shows the pressure reducing valve of FIG. 5*a* with the flexible cuff illustrated in a first position.
Figure 5C:
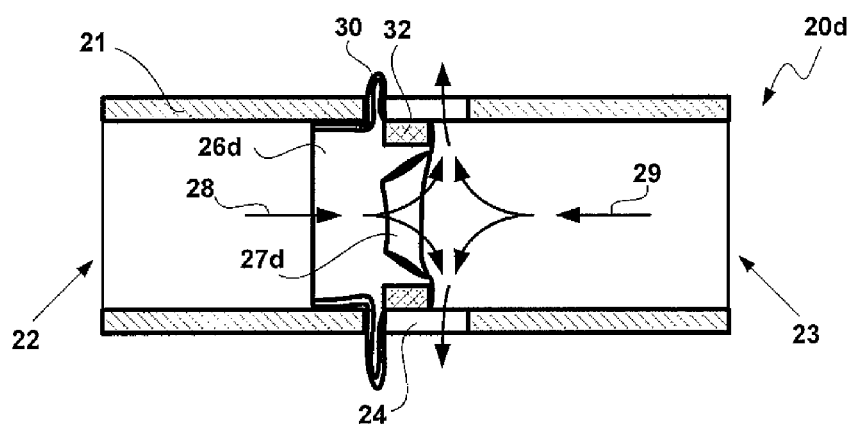
FIG. 5*c* shows the pressure reducing valve of FIG. 5*a* with the flexible cuff illustrated in a second position.

Referring now to FIGS. 5a-5c, a pressure reducing valve 20d according to another embodiment is illustrated. Pressure reducing valve 20d includes a valve body 21 and a flexible cuff 25d. Valve body 21 is substantially the same the valve body of pressure reducing valve 20a (e.g., has a pressure generating end 22, a patient interface end 23, and a number of exhaust ports 24 therebetween).

Flexible cuff 25d includes a first end 26d and a second end 27d. In the current embodiment, first end 26d is coupled to the interior of valve body 21. Accordingly, first end 26d remains stationary relative to valve body 21 when flexible cuff 25d alternates between a first position (see FIG. 5b) and a second position (see FIG. 5c). Flexible cuff 25d also includes a bellows portion 30 and an insert 32 between first end 26d and second end 27d. In the current embodiment, insert 32 is constructed of a semi-rigid material although other types of materials are contemplated.

During the inspiratory phase of a breathing cycle, as shown in FIG. 5b, flexible cuff 25d is in the first position. Bellows portion 30 and insert 32 substantially occlude exhaust ports 24 such that flow of breathing gas 28 is not discharged therethrough. Additionally, as seen in FIG. 5b, second end 27d of flexible cuff 25d is structured to expand such that flow of breathing gas 28 flows more freely from pressure generating end 22 to patient interface end 23.

During the expiratory phase of a breathing cycle, flexible cuff 25d is in the second position. Referring to FIG. 5c, flow of exhaled gas 29 causes flexible cuff 25d to collapse such that second end 27d folds back (e.g., deforms and reverses) towards first end 26b. As seen in FIG. 5c, insert 32 limits the distance that second end 27d collapses relative to first end 26d and may also limit the amount to which exhaust ports 24 are opened. In this second position, however, exhaust ports 24 are opened enough to allow flow of breathing gas 28 and flow of exhaled gas 29 to be discharged therethrough. Because flow of breathing gas 28 is discharged to atmosphere, the patient experiences a temporary drop in positive airway pressure. At the end of the expiratory phase, flow of exhaled gas 29 ceases, the patient begins to inhale, and the flexible cuff 25d returns to the first position.

In the current embodiment, bellows portion 30 is structured to generate a slight biasing force which assists the flexible cuff 25d in returning to the first position. It is contemplated that the material of construction and/or the size of insert 32 may be selected so as to adjust the amount of breathing gas 28 and exhaled gas 29 that are discharged through exhaust ports 24, thus controlling the amount of positive airway pressure drop experienced by the patient.

Figure 6A:
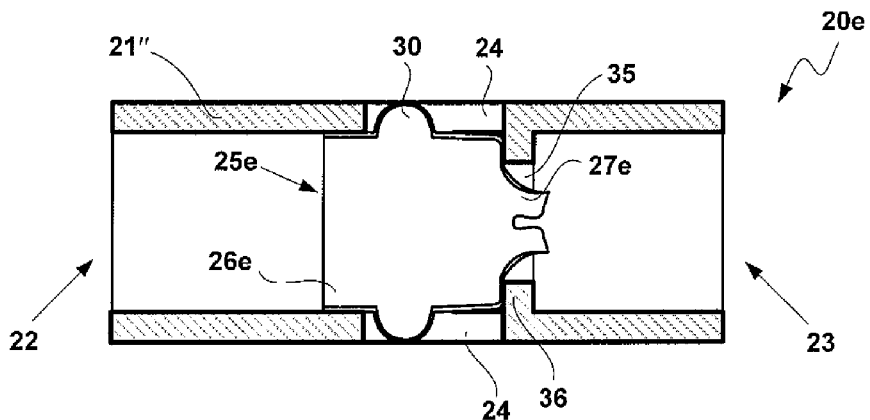
FIG. 6*a* is a cross-sectional view of a pressure reducing valve according to another embodiment.
Figure 6B:
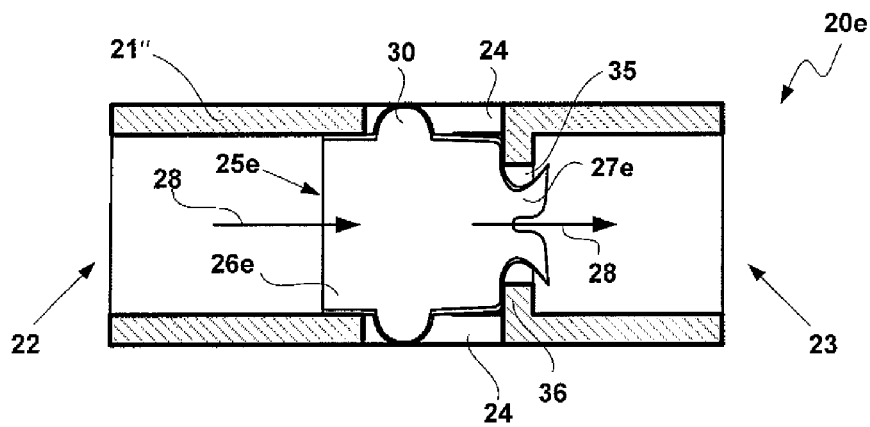
FIG. 6*b* shows the pressure reducing valve of FIG. 6*a* with the flexible cuff illustrated in a first position.
Figure 6C:
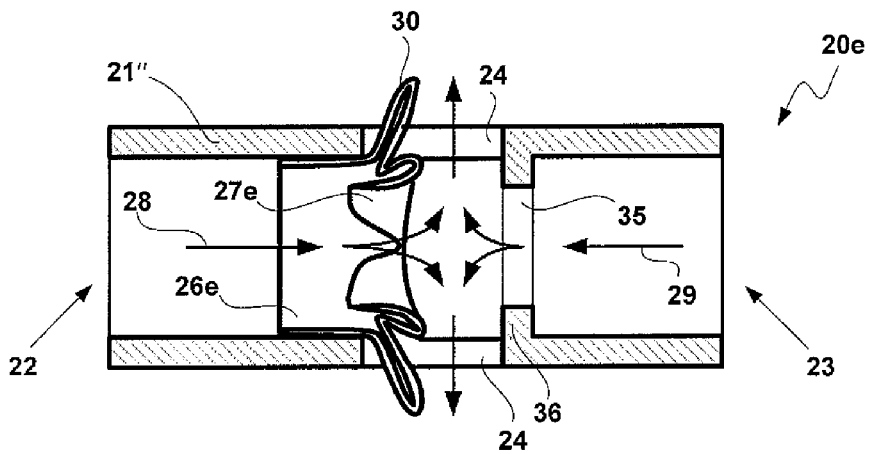
FIG. 6*c* shows the pressure reducing valve of FIG. 6*a* with the flexible cuff illustrated in a second position.

Referring now to FIGS. 6a-6c, a pressure reducing valve 20e according to another embodiment is illustrated. Pressure reducing valve 20e includes a valve body 21" and a flexible cuff 25e. Valve body 21" has a pressure generating end 22, a patient interface end 23, and a number of exhaust ports 24 therebetween. Valve body 21" also includes a seat 36 defining an orifice 35.

Flexible cuff 25e includes a first end 26e and a second end 27e. In the current embodiment, first end 26e is coupled to the interior of valve body 21". Accordingly, first end 26e remains stationary relative to valve body 21" when flexible cuff 25e alternates between a first position (see FIG. 6b) and a second position (see FIG. 6c). Second end 27e includes a notched portion adapted to allow flexible cuff 25e to more easily collapse to the second position. Flexible cuff 25e also includes a bellows portion 30 between first end 26e and second end 27e. Bellows portion 30 is structured to generate a slight biasing force which assists the flexible cuff 25e in returning to the first position.

During the inspiratory phase of a breathing cycle, as shown in FIG. 6b, flexible cuff 25e is in the first position. Bellows portion 30 substantially occludes exhaust ports 24 and a portion of flexible cuff 25e contacts seat 36 such that flow of breathing gas 28 is not discharged through exhaust ports 24.

Additionally, as seen in FIG. 6b, second end 27e of flexible cuff 25e is structured to expand such that flow of breathing gas 28 flows more freely from pressure generating end 22 to patient interface end 23. As shown in FIG. 6b, second end 27e may extend through orifice 35.

During the expiratory phase of a breathing cycle, flexible cuff 25e is in the second position. Referring to FIG. 6c, flow of exhaled gas 29 causes flexible cuff 25e to collapse such that second end 27e folds back (e.g., deforms and reverses) towards first end 26e. As seen in FIG. 5c, when in the second position, the portion of flexible cuff 25e is no longer in contact with seat 36 and exhaust ports 24 are opened to allow flow of breathing gas 28 and flow of exhaled gas 29 to be discharged therethrough. Because flow of breathing gas 28 is discharged to atmosphere, the patient experiences a temporary drop in positive airway pressure. At the end of the expiratory phase, flow of exhaled gas 29 ceases, the patient begins to inhale, and the flexible cuff 25e returns to the first position.

Referring now to FIGS. 7a-7e, a pressure reducing valve 20f according to another embodiment is illustrated. Pressure reducing valve 20f includes a valve body 21 and a flexible cuff 25f. Valve body 21 is substantially the same the valve body of pressure reducing valve 20a (e.g., has a pressure generating end 22, a patient interface end 23, and a number of exhaust ports 24 therebetween).

Flexible cuff 25f includes a first end 26f and a second end 27f. In the current embodiment, first end 26f is coupled to the interior of valve body 21. Accordingly, first end 26f remains stationary relative to valve body 21 when flexible cuff 25f alternates between a first position (see FIG. 7b) and a second position (see FIG. 7c). Flexible cuff 25f also includes a bellows portion 30 between first end 26f and second end 27f. Bellows portion 30 is structured to generate a slight biasing force which assists the flexible cuff 25f in returning to the first position. At second end 27f, flexible cuff 25f further includes a hi-directional flap 33 which partially occludes an inner orifice 34.

Figure 7A:
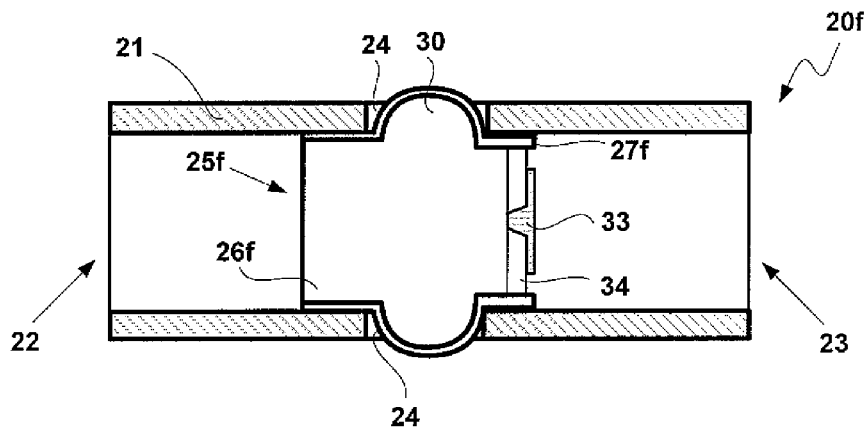
FIG. 7*a* is a cross-sectional view of a pressure reducing valve according to another embodiment.
Figure 7B:
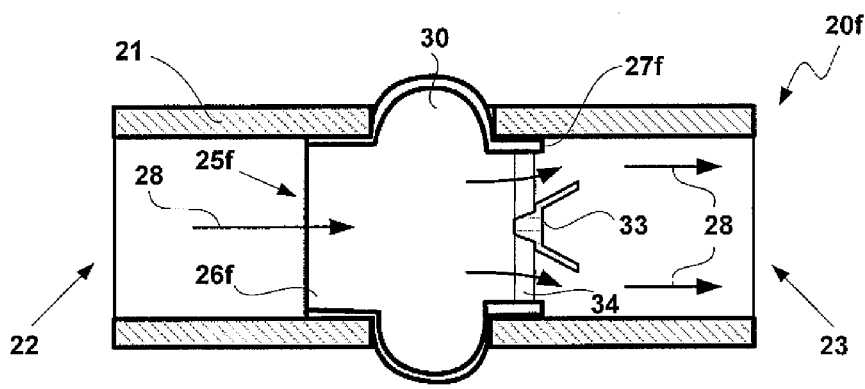
FIG. 7*b* shows the pressure reducing valve of FIG. 7*a* with the flexible cuff illustrated in a first position.

During the inspiratory phase of a breathing cycle, as shown in FIG. 7b, flexible cuff 25f is in the first position. Bellows portion 30 substantially occludes exhaust ports 24 such that flow of breathing gas 28 it not discharged through exhaust ports 24. Additionally, bi-directional flap 33 flexes towards patient interface end 23, thereby expanding the size of inner orifice 34 such that flow of breathing gas 28 flows more freely from pressure generating end 22 to patient interface end 23.

Figure 7C:
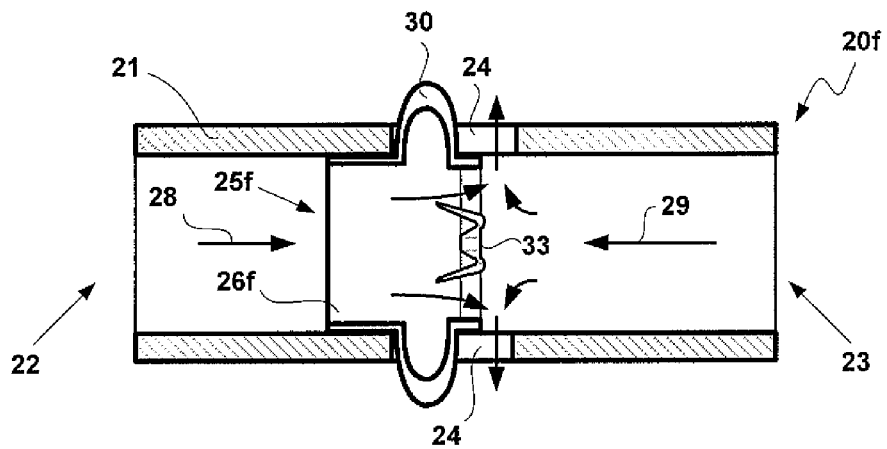
FIG. 7*c* shows the pressure reducing valve of FIG. 7*a* with the flexible cuff illustrated in a second position.

During the expiratory phase of a breathing cycle, flexible cuff 25f is in the second position. Referring to FIG. 7c, flow of exhaled gas 29 causes bi-directional flap 33 to flex towards pressure generating end 22 and further causes bellow 30 to collapse such that second end 27f is pushed back towards first end 26f. In this second position, exhaust ports 24 are opened to allow flow of breathing gas 28 and flow of exhaled gas 29 to be discharged therethrough. Because flow of breathing gas 28 is discharged to atmosphere, the patient experiences a temporary drop in positive airway pressure. At the end of the expiratory phase, flow of exhaled gas 29 ceases, the patient begins to inhale, and the flexible cuff 25f returns to the first position.

Figure 8A:
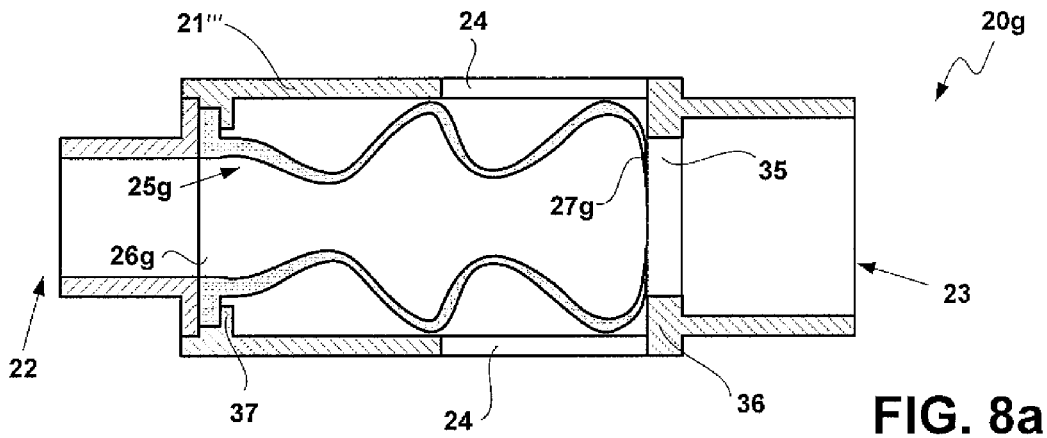
FIG. 8*a* is a cross-sectional view of a pressure reducing valve according to another embodiment.
Figure 8B:
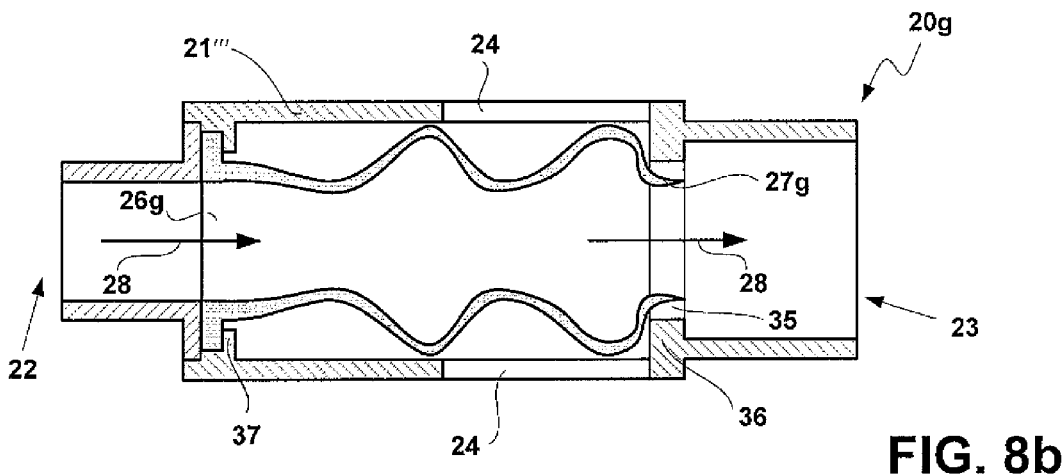
FIG. 8*b* shows the pressure reducing valve of FIG. 8*a* with the flexible cuff illustrated in a first position.
Figure 8C:
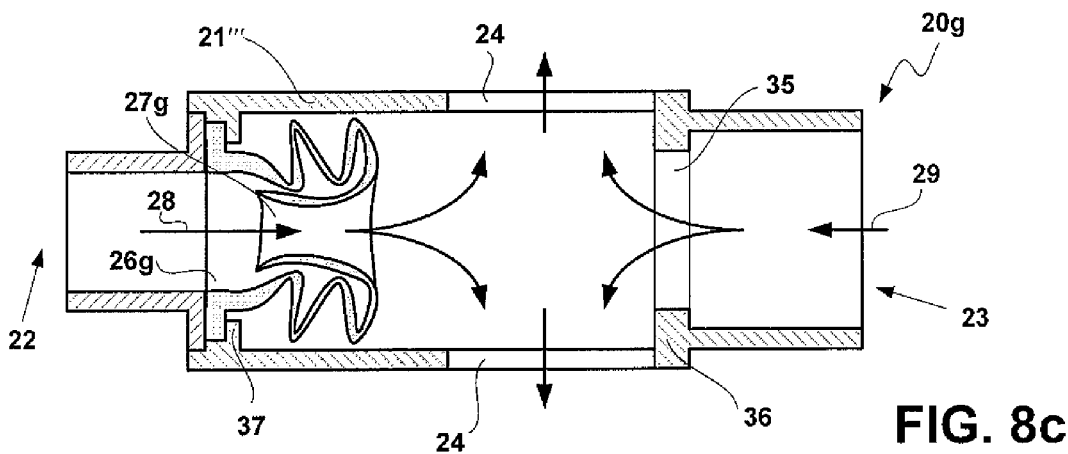
FIG. 8*c* shows the pressure reducing valve of FIG. 8*a* with the flexible cuff illustrated in a second position.

Referring now to FIGS. 8a-8c, a pressure reducing valve 20g according to another embodiment is illustrated. Pressure reducing valve 20g includes a valve body 21''' and a flexible cuff 25g. Valve body 21''' has a pressure generating end 22, a patient interface end 23, and a number of exhaust ports 24 therebetween. Valve body 21''' also includes a seat 36, defining an orifice 35, and a lip 37.

Flexible cuff 25g includes a first end 26g and a second end 27g. In the current embodiment, first end 26g is coupled to the interior of valve body 21''' by lip 37. Accordingly, first end 26g remains stationary relative to valve body 21''' when flexible cuff 25g alternates between a first position (see FIG. 8b) and a second position (see FIG. 8c).

During the inspiratory phase of a breathing cycle, as shown in FIG. 8b, flexible cuff 25g is in the first position. In this first position, flexible cuff 25g substantially occludes exhaust ports 24 and a portion of flexible cuff 25g is in contact with seat 36 such that flow of breathing gas 28 is not discharged through exhaust ports 24. Additionally, second end 27g of flexible cuff 25g is structured to expand such that flow of breathing gas 28 flows more freely from pressure generating end 22 to patient interface end 23. As shown in FIG. 8b, second end 27g may extend within orifice 35.

During the expiratory phase of a breathing cycle, flexible cuff 25g is in the second position. Referring to FIG. 8c, flow of exhaled gas 29 causes flexible cuff 25g to collapse such that second end 27g folds back (e.g., deforms and reverses) towards first end 26g. As seen in FIG. 8c, when in the second position, a portion of flexible cuff 25g is no longer in contact with seat 36 and exhaust ports 24 are opened to allow flow of breathing gas 28 and flow of exhaled gas 29 to be discharged therethrough. Because flow of breathing gas 28 is discharged to atmosphere, the patient experiences a temporary drop in positive airway pressure. At the end of the expiratory phase, flow of exhaled gas 29 ceases, the patient begins to inhale, and the flexible cuff 25g returns to the first position.

Although a bellows is employed as biasing member in FIGS. 3, 5, 6, and 7, it is contemplated that other biasing members (such as, without limitation: a spring, a magnets, etc.) may be used while remaining within the scope of the present invention. Furthermore, although illustrated as aiding the flexible cuff to return to the first position in FIGS. 3, 5, 6, and 7, it is contemplated that the biasing force may be reverse to aid the flexible cuff to return to the second position while remaining within the scope of the present invention.

Figure 9:
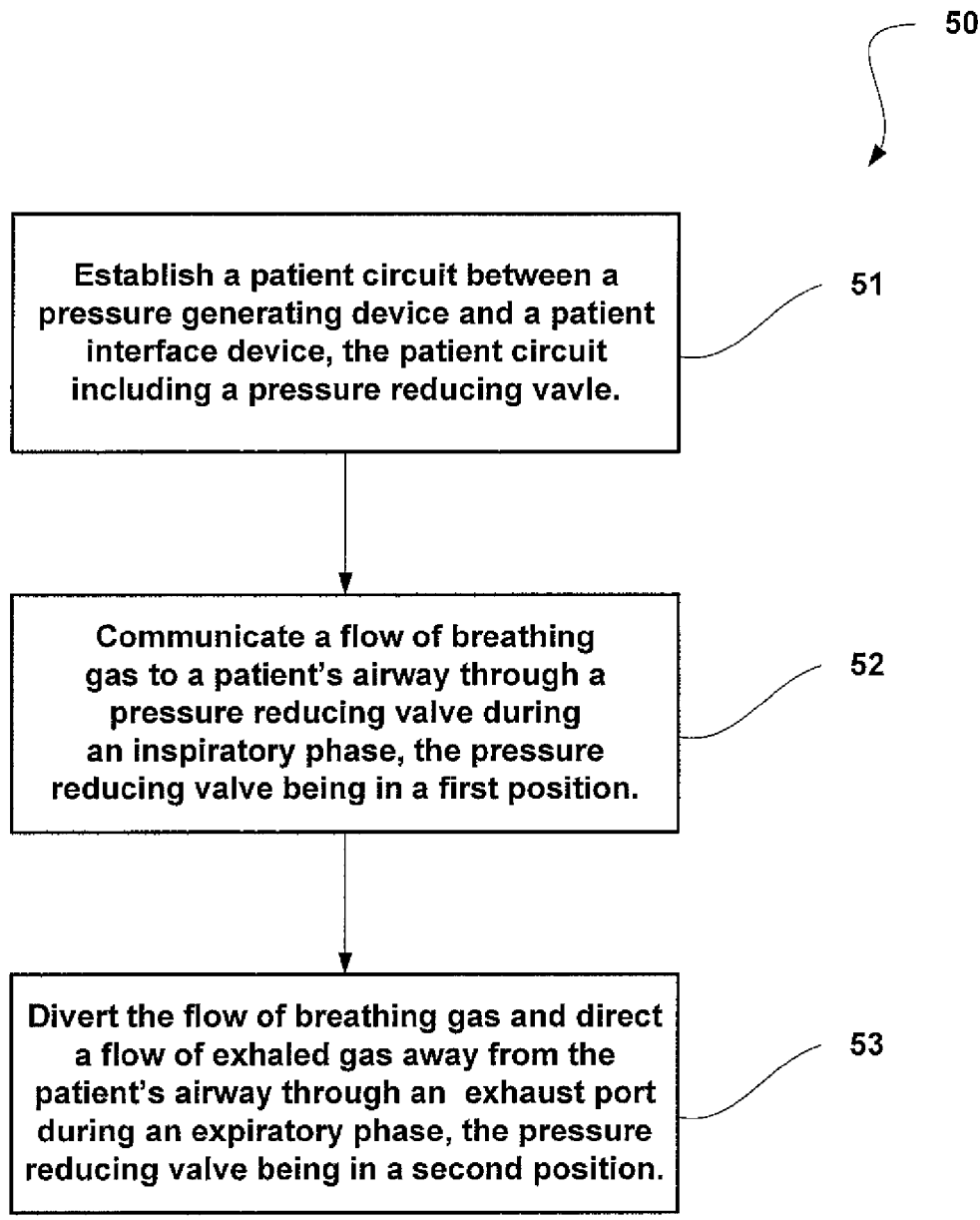
FIG. 9 illustrates an operational process for ventilating a patient according to one embodiment.

FIG. 9 illustrates an operational process 50 for providing a breathing gas to a patient. Operational process 50 begins with operation 51 in which a patient circuit between a pressure generating device and a patient interface device is established. In the current embodiment, for example, a patient circuit 12 with a conduit 14 and pressure reducing valve 20 is established between pressure generating device 13 and patient interface device 15. As discussed above, a pressure reducing valve according to the present invention includes a valve body and a flexible cuff; the valve body having a pressure generating end 22, a patient interface end 23, and a number of exhaust ports 24.

After the patient circuit is established, operational control then passes to operation 52 where a flow of breathing gas is communicated to the patient's airway during an inspiratory phase. In the current embodiment, pressure generating device 13 produces a flow of breathing gas 28 which is communicated to the patient's airway via a patient interface device 15; the pressure generating device 13 and patient interface device 15 being fluidly coupled via the patient circuit 12 established in operation 51. During the inspiratory phase, the pressure reducing valve 20 is in a first position in which the flexible cuff 25 is structured to occlude exhaust ports 24 while providing an open path between the pressure generating end 22 and the patient interface end 23. Accordingly while in the first position, pressure reducing valve 20 is structured to allow free communication of the flow of breathing gas 28 from the pressure generating device 13 to the patient interface device 15 while preventing the flow of breathing gas 28 from being discharged through exhaust ports 24.

After the flow of breathing gas is communicated to the patient's airway during the inspiratory phase, operational control passes to operation 53 where the flow of breathing gas and a flow of exhaled gas are directed away from the patient's airway. In the current embodiment, the pressure reducing valve 20 changes from the first position to a second position in which the flexible cuff 25 is structured to collapse such that exhaust ports 24 are opened while also providing an open path between the pressure generating end 22 and the patient interface end 23. Accordingly while in the second position, pressure reducing valve 20 is structured to allow flow of breathing gas 28 and flow of exhaled gas 29 to be discharged through the exhaust ports 24.

It should be apparent to one skilled in the art that operations 52 and 53 may be repeated as the pressure reducing valve 20 alternates between the first position and the second position in response to the patient's breathing cycle.

Figure 10:
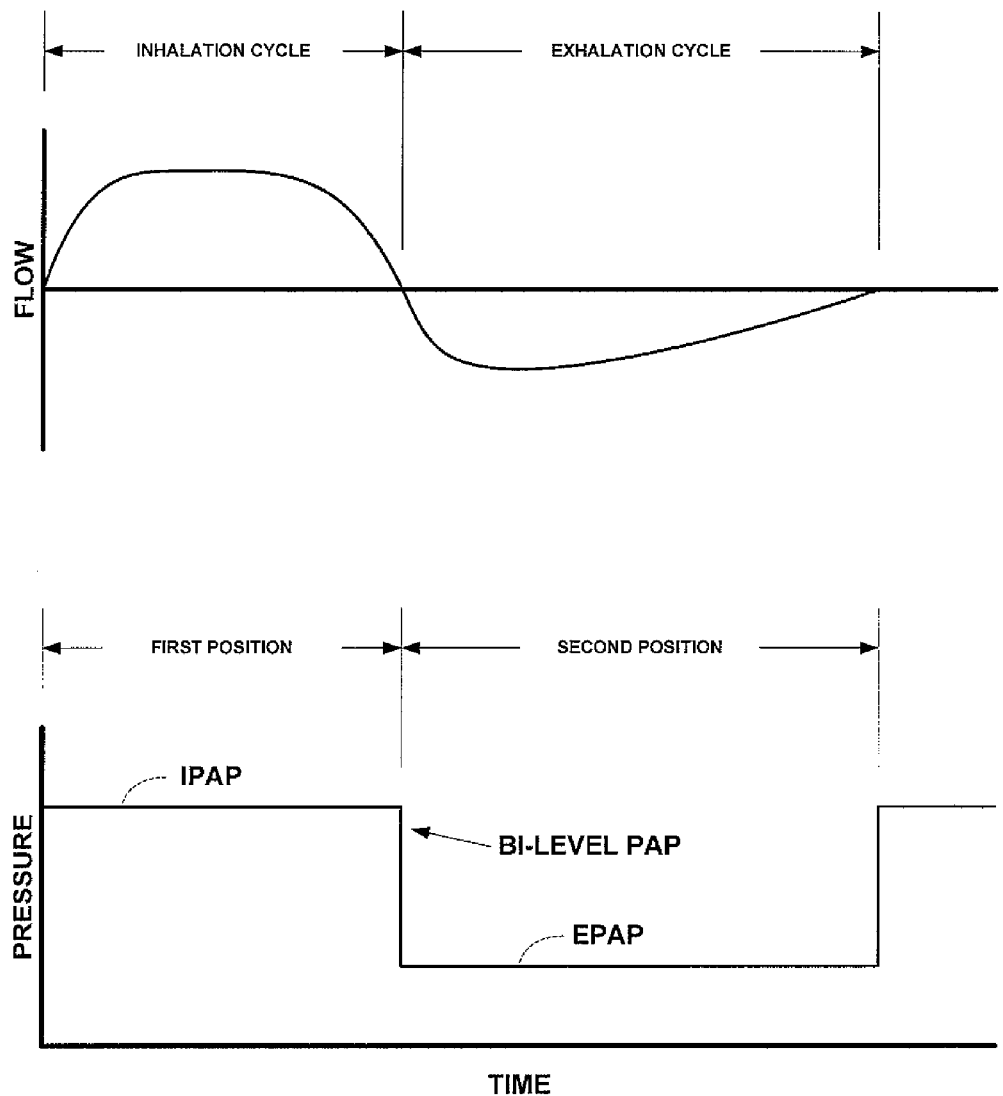
FIGS. 10-12 are various flow/pressure curves illustrating the operation of the pressure reducing valves of the present invention.
Figure 11:
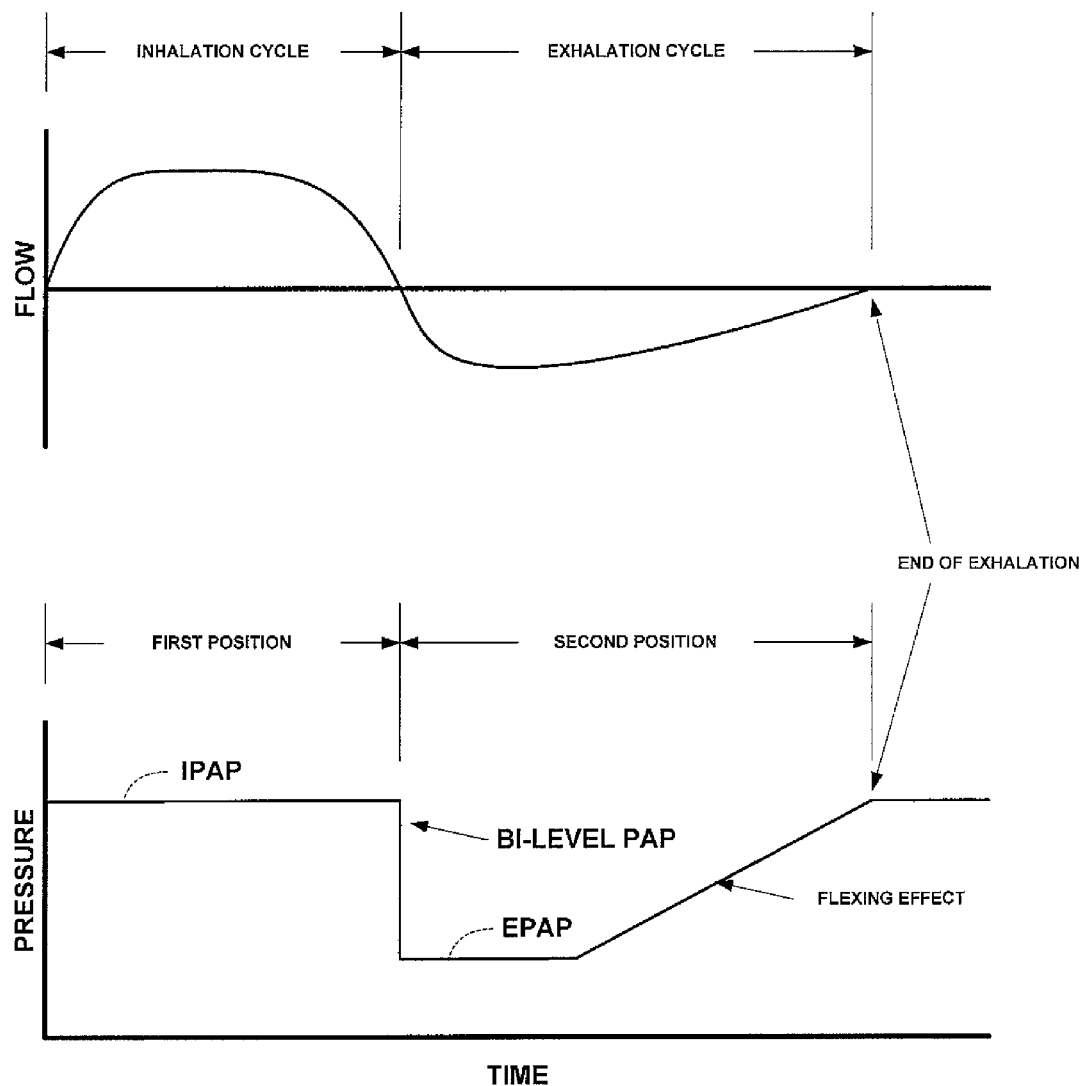
Figure 12:
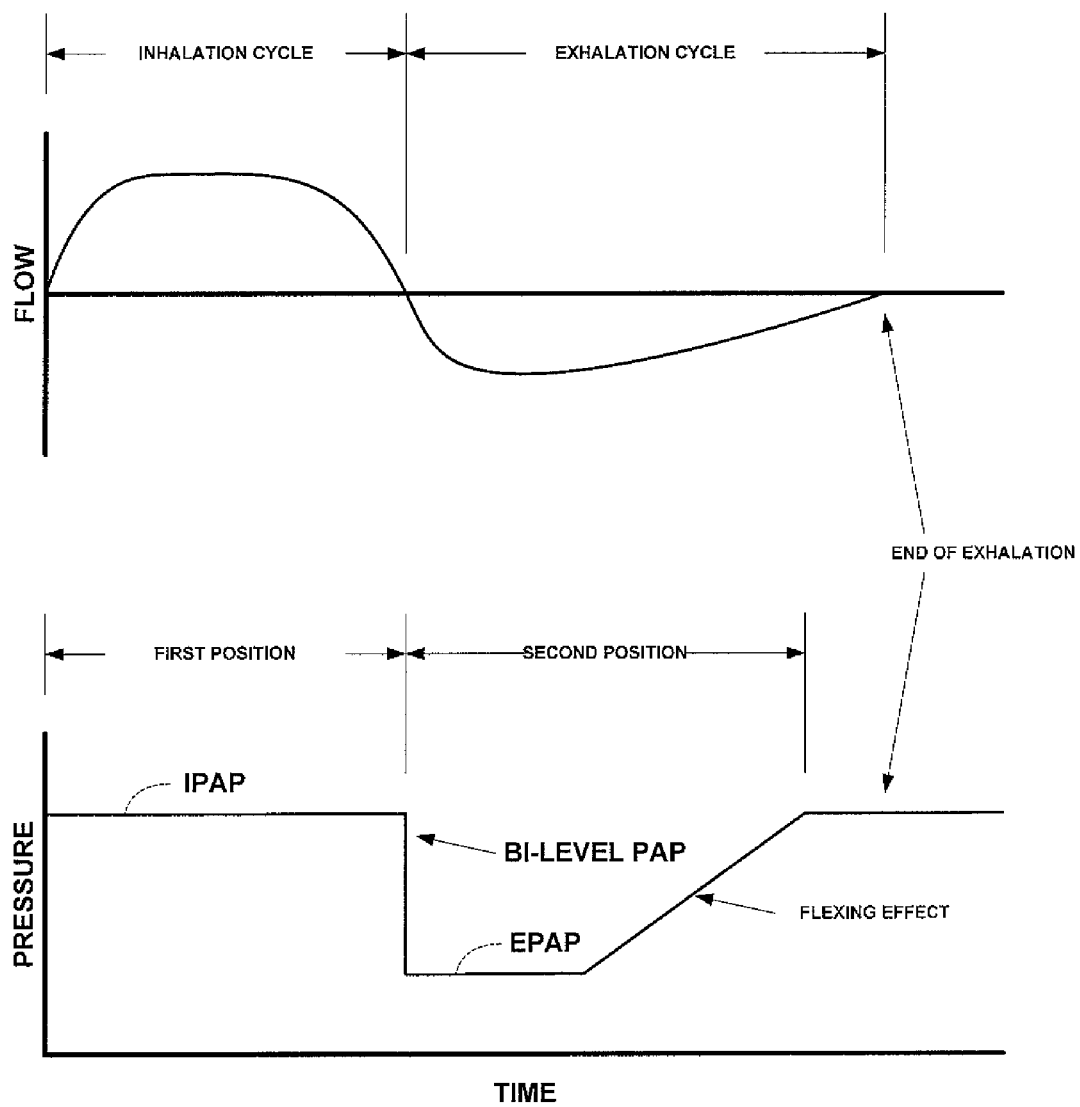

FIGS. 10-12 illustrated flow and pressure curves output by pressure reducing valves of the present invention when, for example, used in system 10 (FIG. 1) with the pressure generating device 13 producing a flow of breathing gas 28 at a constant positive pressure. Although discussed in conjunction with a CPAP pressure generating device 13 (which produces the flow of breathing gas 28 at a constant positive pressure), it is contemplated that other types of pressure generating devices may be employed. The bi-level PAP curves illustrated in FIGS. 10-12 are generated by pressure reducing valves of the present invention.

Referring to FIG. 10, when the pressure reducing valve (for example, pressure reducing valve 20a) is in the first position, the inspiratory positive air pressure is equal to the constant positive air pressure (i.e., IPAP=CPAP) produced by the pressure generating device. When the pressure reducing valve is in the second position, the expiratory positive air pressure is less than the constant positive air pressure (i.e., EPAP<CPAP) because the flow of breathing gas is dumped through exhaust ports. The expiratory positive air pressure level is dependent upon, among others, the size of exhaust ports (and thus the amount of the flow of breathing gas that can be discharge).

FIGS. 11 and 12 illustrate flow and a pressure curves corresponding to the output of a pressure reducing valve having a biasing member (for example, pressure reducing valve 20b) structured to cause the flexible cuff to return to the first position. As seen in FIGS. 11 and 12, the biasing member urges the flexible cuff to move to the first position prior to the end of the exhalation cycle; thus providing a flexing or dampening effect during exhalation. As seen in FIG. 11, the biasing member is structured to cause the pressure reducing valve to close at the end of the exhalation cycle; whereas in FIG. 12, the biasing member is structured to cause the pressure reducing valve to close prior to the end of the exhalation period.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure reducing valve, comprising:
    a valve body with a first end, a second end, and a number of exhaust ports therebetween; and
    a flexible cuff adapted to alternate between a first position in which the number of exhaust ports are substantially closed and a second position in which the number of exhaust ports are substantially open,
    wherein, when the flexible cuff is in the first position, the pressure reducing valve is structured to fluidly communicate a flow of breathing gas from the first end to the second end, and wherein, when the flexible cuff is in the second position: (i) the flexible cuff is deformed and reversed and folded back and bent over upon itself to comprise overlapping portions, and (ii) the pressure reducing valve is structured to fluidly communicate the flow of breathing gas from the first end to the number of exhaust ports and fluidly communicate a flow of exhaled gas from the second end to the number of exhaust ports.

2. The pressure reducing valve of claim 1, wherein the flexible cuff includes a first end and a second end, wherein the first end remains stationary relative to the valve body when the flexible cuff alternates between the first position and the second position.

3. The pressure reducing valve of claim 2, wherein the second end of the flexible cuff is adapted to expand in response to the presence of the flow of breathing gas and the absence of the flow of exhaled gas.

4. The pressure reducing valve of claim 2, wherein the second end of the flexible cuff is adapted to collapse in response to the presence of the flow of exhaled gas.

5. The pressure reducing valve of claim 1, wherein the flexible cuff is structured to alternate from the first position to the second position in response to the beginning of the expiratory phase of a patient's breathing cycle.

6. The pressure reducing valve of claim 1, wherein the flexible cuff is structured to alternate from the second position to the first position in response to the beginning of the inspiratory phase of a patient's breathing cycle.

7. The system of claim 1 wherein the flexible cuff includes a number of bellows.

8. The system of claim 1 wherein the flexible cuff includes a groove adapted to facilitate the transition from the first position to the second position.

9. The system of claim 1 wherein the flexible cuff includes semi-rigid insert.

10. The pressure reducing valve of claim 1, wherein the first end of the valve body is structured to couple with a pressure generating device and wherein the second end of the valve body is structured to couple with a patient interface device.

11. The pressure reducing valve of claim 10, wherein the first end of the valve body is adapted to receive the flow of breathing gas from the pressure generating device and the second end of the valve body is adapted to deliver the flow of breathing gas to a patient and to receive the flow of exhaled gas from such patient.

12. The pressure reducing valve of claim 1, wherein the number of exhaust ports are structured to operatively communicate the flow of breathing gas and the flow of exhaled gas from the interior of the valve body to the exterior of the valve body.

13. The pressure reducing valve according to claim 1, wherein when the flexible cuff is in the second position the overlapping portions still cover and occlude a portion of the number of exhaust ports.

14. A pressure reducing valve, comprising:
a valve body having a patient interface end and a pressure generator end with a number of exhaust ports therebetween; and
a flexible cuff actuatable within the valve body between a first position in which the number of exhaust ports are substantially closed and a second position in which the number of exhaust ports are substantially open, wherein, when the flexible cuff is in the first position, the flexible cuff is structured to allow communication of a flow of breathing gas from the pressure generator end to the patient interface end during a breathing cycle inspiratory phase, and wherein, when the flexible cuff is in the second position: (i) the flexible cuff is deformed and reversed and folded back and bent over upon itself to comprise overlapping portions, and (ii) the flexible cuff is structured to allow communication of the flow of breathing gas and a flow of exhaled gas through the number of exhaust ports during a breathing cycle expiratory phase.

15. The pressure reducing valve of claim 14, wherein the flexible cuff includes a first end and a second end, wherein the first end remains stationary relative to the valve body when the flexible cuff alternates between the first position associated with the breathing cycle inspiratory phase and the second position associated with the breathing cycle expiratory phase.

16. The pressure reducing valve of claim 15, wherein the second end of the flexible cuff is adapted to expand during at least a portion of the breathing cycle inspiratory phase.

17. The pressure reducing valve of claim 15, wherein the second end of the flexible cuff is adapted to collapse during at least a portion of the breathing cycle expiratory phase.

18. The system of claim 14 wherein the flexible cuff includes a number of bellows.

19. The system of claim 14 wherein the flexible cuff includes a groove adapted to facilitate the transition from the first position to the second position.

20. The system of claim 14 wherein the flexible cuff includes semi-rigid insert.

21. The pressure reducing valve of claim 14, wherein the pressure generator end is structured to couple with a pressure generating device operable to produce the flow of breathing gas, and wherein the patient interface end is structured to couple with a patient interface device operable to deliver the flow of breathing gas to a patient's airway and operable to receive the flow of exhaled gas from such a patient's airway.

22. The pressure reducing valve of claim 14, wherein the number of exhaust ports are structured to operatively communicate the flow of breathing gas and the flow of exhaled gas from the interior of the valve body to the exterior of the valve body.

23. The pressure reducing valve according to claim 14, wherein when the flexible cuff is in the second position the overlapping portions still cover and occlude a portion of the number of exhaust ports.

24. A method for ventilating a patient, comprising:
establishing a patient circuit between a pressure generating device and an airway of a patient, the patient circuit including a pressure reducing valve comprising:
a valve body with a first end, a second end, and a number of exhaust ports therebetween; and
a flexible cuff adapted to alternate between a first position in which the number of exhaust ports are substantially closed and a second position in which the number of exhaust ports are substantially open;
communicating a flow of the breathing gas through the patient circuit to the airway of such patient during an inspiratory stage, wherein during the communicating the flexible cuff is in the first position and the pressure reducing valve is structured to fluidly communicate the flow of breathing gas from the first end to the second end; and
diverting the flow of the breathing gas and directing a flow of exhaled gas away from the airway of such patient during an expiratory phase, wherein during the diverting and the directing: (i) the flexible cuff is in the second position and is deformed and reversed and folded back and bent over upon itself to comprise overlapping portions, and (ii) the pressure reducing valve is structured to fluidly communicate the flow of breathing gas from the first end to the number of exhaust ports and fluidly communicate the flow of exhaled gas from the second end to the number of exhaust ports.

25. The method of claim 14, wherein communicating the breathing gas through the patient circuit further comprises generating the flow of breathing gas.

26. The method according to claim 24, wherein when the flexible cuff is in the second position the overlapping portions still cover and occlude a portion of the number of exhaust ports.

27. A system adapted to provide a regimen of respiratory therapy to a patient, comprising:
a pressure generating device structured to produce a flow of breathing gas;
a patient interface device structured to communicate the flow of breathing gas to the airway of a patient and to communicate a flow of exhaled gas from the airway of such patient;
a patient circuit structured to fluidly couple the pressure generating device to the patient interface device; and
a pressure reducing valve disposed between the pressure generating device and the patient interface device, the pressure reducing valve comprising:
a valve body with a number of exhaust ports therein; and
a flexible cuff structured to alternate between a first position in which the flow of breathing gas is communicated from the pressure generating device to the patient interface device, and a second position, in which: (i) the flexible cuff is deformed and reversed and folded back and bent over upon itself to comprise overlapping portions, and (ii) the flow of breathing gas from the pressure generating device and the flow of exhaled gas from the patient interface device are discharged through the number of exhaust ports.

28. The system of claim 27 wherein the pressure generating device includes one of a ventilator, a continuous positive airway pressure device, a variable pressure device, an auto-titration pressure support system, and a compressed air supply.

29. The system of claim 27 wherein the patient interface device includes one of a nasal cannula, a nasal mask, a full face mask, a total face mask, and an endotracheal tube.

30. The system of claim 27 wherein the flexible cuff includes a number of bellows.

31. The system of claim 27 wherein the flexible cuff includes a groove adapted to facilitate the transition from the first position to the second position.

32. The system of claim 27 wherein the flexible cuff includes semi-rigid insert.

33. The system according to claim 27, wherein when the flexible cuff is in the second position the overlapping portions still cover and occlude a portion of the number of exhaust ports.

34. An apparatus for delivering a flow of breathing gas to an airway of a patient, the apparatus comprising:
- a pressure generating means for producing the flow of breathing gas;
- a patient interface means for communicating the flow of breathing gas to the airway of a patient and for communicating a flow of exhaled gas from the airway of such patient; and
- a patient circuit structured to fluidly couple the pressure generating means to the patient interface means, the patient circuit including a pressure reducing valve comprising:
  - a valve body with a number of exhaust ports therein; and
  - a flexible cuff means for alternating between a first position, in which the flow of breathing gas is communicated from the pressure generating means to the patient interface means, and a second position, in which: (i) the flexible cuff is deformed and reversed and folded back and bent over upon itself to comprise overlapping portions, and (ii) the flow of breathing gas from the pressure generating means and the flow of exhaled gas from the patient interface means are discharged through the number of exhaust ports.

35. The apparatus according to claim 24, wherein when the flexible cuff is in the second position the overlapping portions still cover and occlude a portion of the number of exhaust ports.

* * * * *